United States Patent [19]

Whealin

[11] Patent Number: 5,125,917
[45] Date of Patent: Jun. 30, 1992

[54] OSTOMY APPLIANCES

[76] Inventor: William Whealin, 1642 Minnesota Rd., Camden, N.J. 08104-3126

[21] Appl. No.: 637,462

[22] Filed: Jan. 4, 1991

[51] Int. Cl.⁵ .............................................. A61F 5/44
[52] U.S. Cl. .................................... 604/340; 604/332
[58] Field of Search .................................. 604/332-345

[56] References Cited

U.S. PATENT DOCUMENTS

| | | | |
|---|---|---|---|
| 2,869,548 | 8/1955 | Mason | 604/342 |
| 3,495,592 | 2/1970 | Herman | 128/283 |
| 3,570,490 | 3/1971 | Berger | 128/283 |
| 4,219,023 | 8/1980 | Galindo | 128/283 |
| 4,344,434 | 8/1982 | Robertson | 128/283 |
| 4,411,659 | 10/1983 | Jensen et al. | 604/332 |
| 4,419,100 | 12/1983 | Alexander | 604/339 |
| 4,460,363 | 7/1984 | Steer et al. | 604/336 |
| 4,865,594 | 9/1989 | Thomas | 604/332 |

FOREIGN PATENT DOCUMENTS

| | | |
|---|---|---|
| 719111 | 10/1965 | Canada . |
| 2843-930 | 7/1980 | Fed. Rep. of Germany . |
| 2198954 | 6/1988 | United Kingdom . |

OTHER PUBLICATIONS

Instructions for use of sur-fit disposable convex inserts, revised 8/86.

Primary Examiner—Randall L. Green
Assistant Examiner—R. Clarke
Attorney, Agent, or Firm—Simpson & Simpson

[57] ABSTRACT

An ostomy appliance having a concave disk insert disposed between the flexible pouch and the faceplate member and designed to reduce the discomfort of prolapse and/or stoma expansion. The invention also includes an ostomy appliance insert for keeping the pressure of clothing from collapsing the ostomy bag against the stoma. The two inserts can most preferably be used in combination to improve comfort of the ostomy appliance user.

8 Claims, 5 Drawing Sheets

FIG. 2
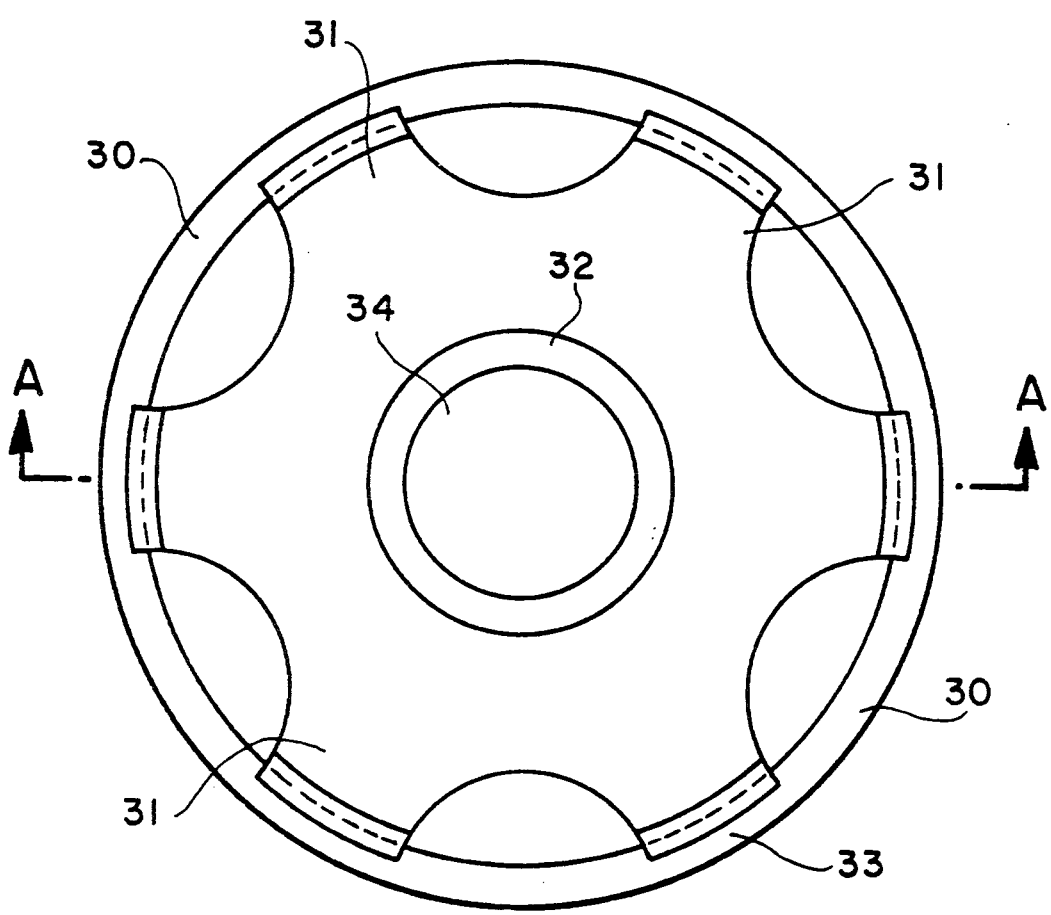
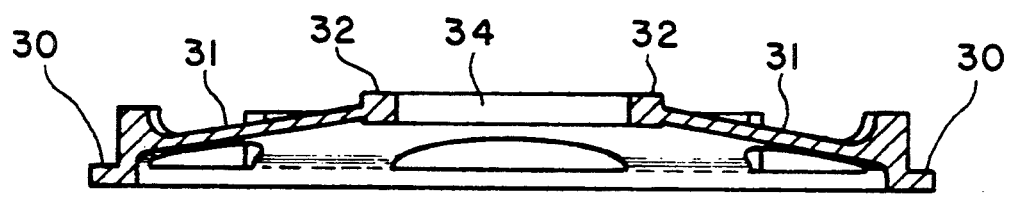
FIG. 2A

OSTOMY APPLIANCES

BACKGROUND OF THE INVENTION

For a number of years ostomy appliances have been available which generally comprise two components, a body-side faceplate assembly, sometimes referred to as body-side wafer or a skin barrier, and a pouch assembly, frequently referred to simply as an ostomy bag. Generally, the body-side faceplate assembly comprises a pad or surgical dressing, a central opening, designed to be adhesively affixed to the skin surface of the user with the stoma passing through the central aperture. The side of the faceplate assembly away from the user is provided with a flange in surrounding relation to the central opening. The ostomy pouch assembly is essentially a waterproof bag affixed with a flanged opening.

The two flanges of the ostomy appliance are matched and mated to provide a coupling between the faceplate assembly and the pouch assembly that will be secure and free of leakage of liquids and gases. U.S. Pat. No. 4,419,100 to Alexander, and U.S. Pat. No. 4,460,363 to Steer and Edwards provide detailed description of both the ostomy appliances and of a variety of coupling flanges that are useful for securing the body-side faceplate assembly and the ostomy pouch assembly to each other. Commercially available examples of these devices include the Hollister Two-piece Ostomy System, manufactured by Hollister Incorporated, Libertyville, Ill., and the Sure-fit System, manufactured by Convatech, a Squibb Company of Princeton, N.J.

While these various ostomy appliances are useful and effective, there is considerable room for improvement in the devices to increase the comfort of the user. In the typical situation, there is a tendency for the stoma to expand in size. As an example, it has been known for the diameter of a stoma to double in size over a period of two years. This requires replacing the central opening in the ostomy faceplate assembly with one of a somewhat larger opening to accommodate the larger stoma. A general discomfort accompanies this expansion of the stoma.

A more serious problem encountered by persons who have had a colostomy and ileostomy or the like is the occurrence of prolapse. During prolapse, there is a tendency for a portion of the organs behind the immediate opening to the stoma to protrude through the open and beyond the stoma. This occurs in a number of ways and in a number of forms but is almost always a matter of substantial discomfort. The only methods known at the present time for relieving prolapse are surgical, usually involving closure of the stoma, and reopening of a stoma at another more suitable location. Temporary relief is frequently obtained by the wearer of the ostomy sevices by placing the hand over the stoma and exerting pressure so as to relieve the effects of the prolapse.

Still another problem encountered by ostomy appliance users results from the pressure of clothing against the exterior of the bag, especially when the ostomy appliance user sits down. The pressure of the clothing against the ostomy bag tends to close off the opening into the bag and/or create a clogging situation.

SUMMARY OF THE INVENTION

This invention is directed to devices for insertion between the coupling flanges of the body-side faceplate assembly and the ostomy pouch assembly which will reduce the tendency for prolapse and/or expansion of the stoma over time, and which will relieve the effects of clothing pressure on the ostomy bag as a source of clogging of the ostomy appliance.

BRIEF DESCRIPTION OF THE DRAWINGS

FIG. 2 is an elevation view of a device for use in combination with the ostomy pouch assembly of FIG. 1 which will reduce the tendency for prolapse and/or expansion of the stoma.

FIG. 2A is a horizontal axial section along the line A—A of the device shown in FIG. 2.

FIG. 4A is used in combination with the embodiment of FIG. 3 and FIG. 3A.

DETAILED DESCRIPTION OF THE DRAWINGS

Figure 1:
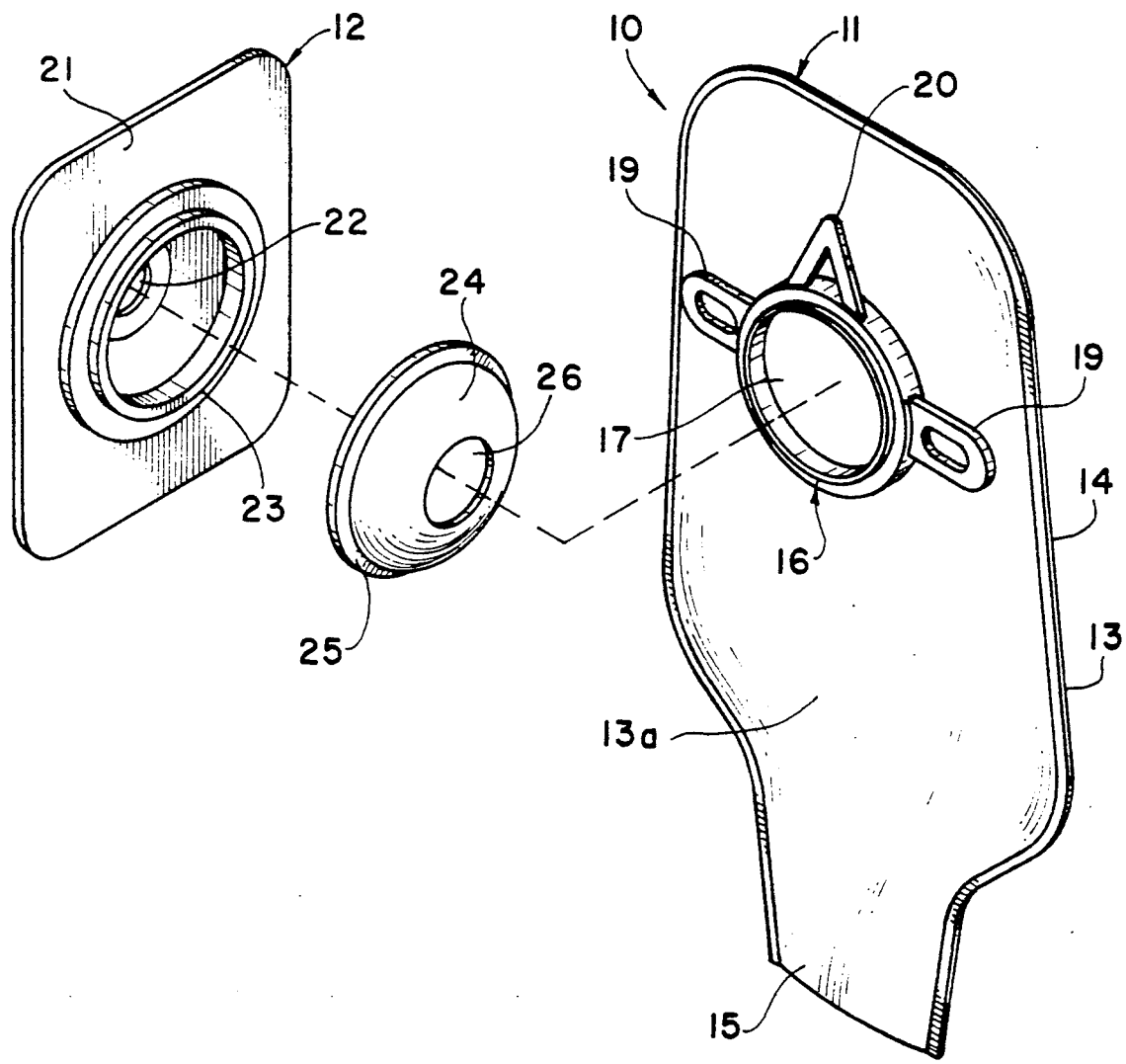
FIG. 1 is a perspective view of the two main components of the ostomy appliance of the prior art, a body-side faceplate assembly and a pouch assembly, such components being depicted in detached condition. Also illustrated is a concave disk that is useful for reducing the discomfort of prolapse and/or extension of the stoma.

FIG. 1 illustrates a two-part ostomy appliance 10 consisting of a pouch assembly 11 and a faceplate assembly 12. The pouch assembly includes a collection pouch 13 which may be formed of two panels, front panel 13a and a back panel (not visible) joined together by a peripheral zone of heat sealing 14 and terminating in an open neck portion 15 at the pouch's lower end. Where such a neck portion is provided, a suitable clamp, such as the clamp disclosed in U.S. Pat. No. 3,523,534, would be used to maintain the pouch's lower end in closed condition. Alternatively, neck portion 15 may be omitted entirely and the heat-sealing zone 14 may extend about the full periphery of the pouch.

A first coupling ring 16 is secured to one wall 13a of the pouch by heat sealing or by any other suitable means. The coupling ring 16 has a generally circular configuration, defining a central opening 17 which communicates with the interior of the pouch through an aperture in the upper portion of panel 13a. A pair of apertured tongues 19 may project laterally from opposite sides of the coupling ring 16 for the attachment of a suitable support belt, if the use of such a belt is desired by the wearer. An integral tab 20 also projects radially outwardly from the periphery of coupling ring 16 to serve as a handle for pulling ring 16 away from the faceplate assembly 12 during an uncoupling operation.

In the embodiment illustrated, the faceplate assembly 12 includes a highly flexible faceplate 21 preferably formed of a gas-penetrable but water resistant microporous material. The faceplate 21 is generally rectangular in outline and is provided with a small central opening 22.

A second coupling ring 23 is mounted upon faceplate 21, adapted to be received within the first coupling ring 16. The insert portion has an integral spring latching member which is engageable with outer wall of ring 16 to perform the dual functions of forming a fluid-tight seal between the parts and of establishing a double-latch that locks the two rings against unintentional disconnection. Examples of such locking mechanisms are illustrated, for example, in U.S. Pat. No. 4,419,100 to Alexander and U.S. Pat. No. 4,468,363 to Steer, et al. The present invention is designed to be used with ostomy appliances of the type illustrated in the foregoing two patents and which utilize a coupling mechanism of the type shown.

Figure 1A:
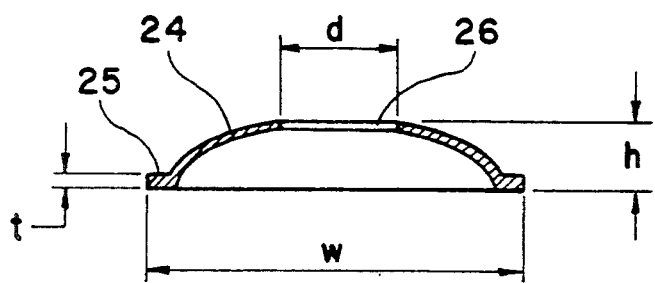
FIG. 1A is a horizontal axial section of the concave disk shown in FIG. 1.

In its simplest form, the device for reducing the tendency for prolapse and/or extension of the stoma, indicated generally in FIG. 1 and FIG. 1A as concave disk 24, is a semi-rigid to rigid, resilient, concave member of thin-walled material that can generally be described as a saucer-shaped disk having a protruding lip 25 at its outermost portions and a central opening 26. The outer diameter "w" of the lip must be greater than the exterior diameter of the smaller of the two coupling rings 16 and 23, but less than the inner diameter of the larger of the coupling rings such that the concave disk 24 may be inserted between the coupling rings and the coupling rings coupled without the concave insert passing through the central open portions of the coupling rings. Care must be exercised to ensure that the thickness "t" of the lip 25 is not so great as to interfere with or preclude defective coupling of the coupling rings. For example, 0.04 inch has been found generally satisfactory. In this way, the concave insert of the present invention can be placed between the coupling rings and coupled and held in place during use. The diameter "d" of the central opening in the concave disk 24 of the present invention should normally fall within the range of about one-half inch up to about three-fourths inch. If the central opening to the concave disk is smaller than one-half inch, it will interfere with the normal operation of the ostomy appliance and the passage of the materials through the stoma into the ostomy bag. If the opening is larger than indicated, the concave disk will provide inadequate support and fail to provide the improvements noted for using the disk. The opening to the concave disk is preferably about five-eighths (⅝) inch in diameter.

While it is necessary that the concave disk be dished, it should not be so concave that it will protrude substantially beyond the plane of juncture of the coupling ring with the ostomy bag. In general, a concave curvature which will provide an overall height "h" of about 0.2 inch is appropriate. The overall height should not be such that the disk protrudes substantially beyond the coupling rings into the ostomy bag. It should be great enough that it does not touch the stoma when the stoma is in its normal (i.e. "nonprolapsed") condition and there should be no undue interference with the normal operation of the ostomy appliance.

The concave disk of the present invention can be made out of any suitable material that is sufficiently rigid to avoid collapsing during usage, but which, nevertheless, has sufficient resilience to absorb shocks of the type normally encountered in the wearing of ostomy appliances. In general, the disk can be made of the same types of materials from which the coupling rings themselves are manufactured.

In its simplest form, therefore, the present invention can be thought of as a concave disk with a central opening generally smaller in diameter than the stoma and a lipped outer portion to be gripped by the coupling rings in a manner that aligns the opening of the stoma with the central opening of the disk. There is a tendency, however, for some of the material discharged from the stoma to accumulate in or around the concave insert. In order to facilitate in-place cleaning and/or to minimize the accumulation of materials, the concave insert is preferably provided with holes or openings which do not interfere with the structural integrity of the insert. Examples of devices with this structure follow.

FIGS. 2 and 2A illustrate an embodiment of the invention which is particularly designed to reduce the tendency to prolapse and/or a tendency for the stoma to expand in size. In this particular embodiment, the concave disk has been provided with openings in a manner to leave a circumferential ring 30 with a plurality of rib portions 31 extending radially inward toward the center of the ring, but away from the plane of the ring to a central reinforcing ring portion 32 which is in surrounding relation to and defines a central opening 34. The device may be machined from a single piece of suitable material to be discussed subsequently, or may be molded or cast or, indeed, may be fabricated from separate parts and joined by appropriate means known to the art to form the unitary structure shown in FIGS. 2 and 2A. It is important when constructing the device of FIGS. 2 and 2A that the rib portions 31 be attached to the circumferential ring 30 in a manner to provide a free lip area indicated generally as 33 in FIG. 2. During normal use, the device of FIG. 2 is placed between the coupling rings 16 and 23 as shown in FIG. 1 in a manner that the coupling rings grip and hold the lip portion 33 in place when the coupling rings are joined to form the unitary ostomy appliance. The reinforcing ring portion 32, while not necessary, can be employed to provide additional strength to the concave disk to resist crushing.

Figure 3:
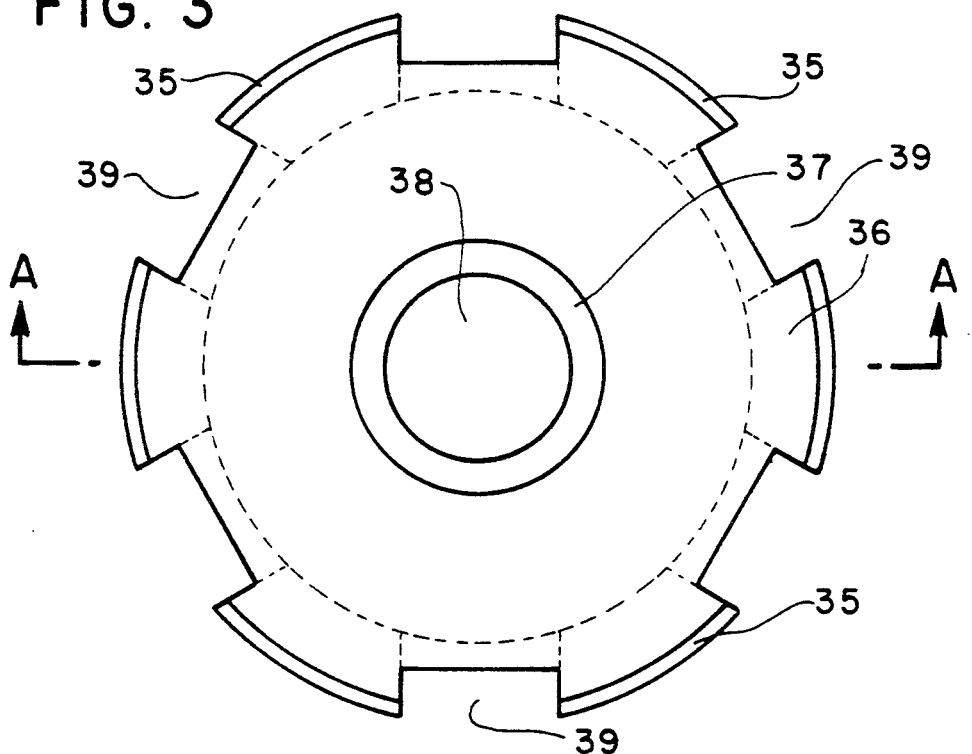
FIG. 3 is an elevation view of a second device for use in combination with the ostomy pouch assembly of FIG. 1 which will reduce the tendency for prolapse and/or expansion of the stoma.
Figure 3A:
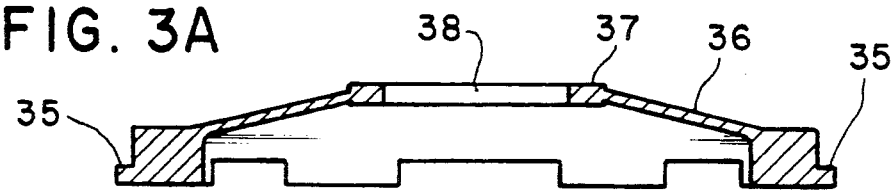
FIG. 3A is a horizontal axial section along the line A—A of the device shown in FIG. 3.

FIGS. 3 and 3A illustrate a second embodiment of the invention. In this embodiment the circumferential ring 30 is replaced by simply a series of circumferentially located lips 35, leaving additional space open between the "rib" portions. The lip portions are of sufficient size to be gripped by the coupling rings of the ostomy appliance. By proper choice of materials to provide a product of sufficient rigidity, the modification of FIG. 3 and FIG. 3A will be as structurally sound as that of FIGS. 2 and 2A. As with the body shown in FIG. 2, the device is preferably provided with a reinforcing or strengthening ring 37, and the concave disk may simply be provided with a continuous surface up to the central opening 38. The advantages of having the spaced openings 39 between lip portions 35 of the device shown in FIG. 3 will be discussed in detail with the embodiment of FIG. 4.

Figure 3B:
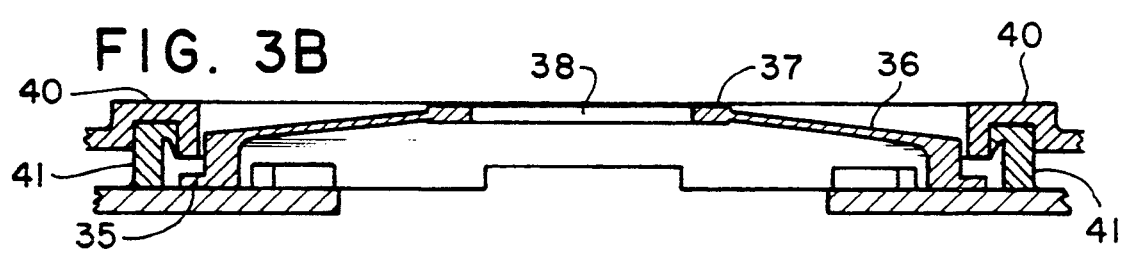
FIG. 3B is a schematic section showing a device of the type of FIG. 3A held in place in an ostomy bag appliance and clamped in place.
Figure 3C:
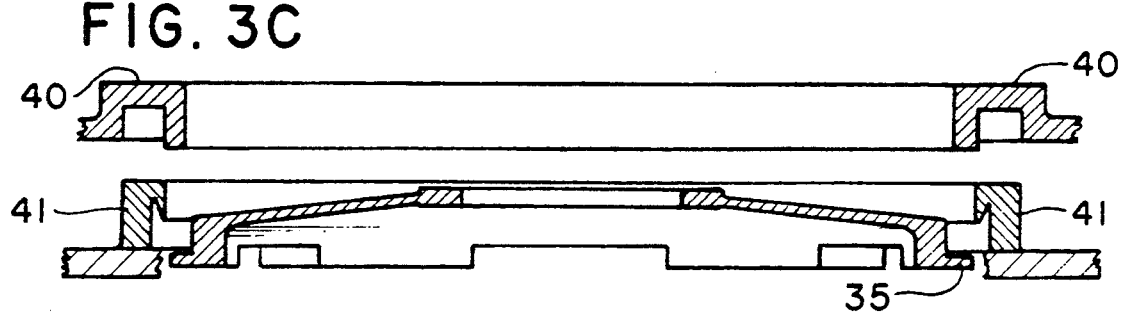
FIG. 3C corresponds generally with FIG. 3B, but in an exploded form and with the two principal parts of the ostomy bag appliance separated to further illustrate the manner in which the device of the present invention fits into the clamping mechanism.

FIGS. 3B and 3C show the device of the present invention held between coupling rings. The portions of the concave disk are numbered in the same manner as they are in FIGS. 3 and 3A. Clamping ring 40 is the ring associated with the ostomy bag. Clamping ring 41 is the ring associated with the faceplate flange. As can be seen by comparing FIGS. 3B and 3C, the clamping rings are provided with suitable mechanisms for gripping each other. When in the closed position they exert pressure on lips 35 and hold the concave disk in place without interfering with the clamping ring mechanism or the uniting of the two major parts of the ostomy appliance.

Figure 4:
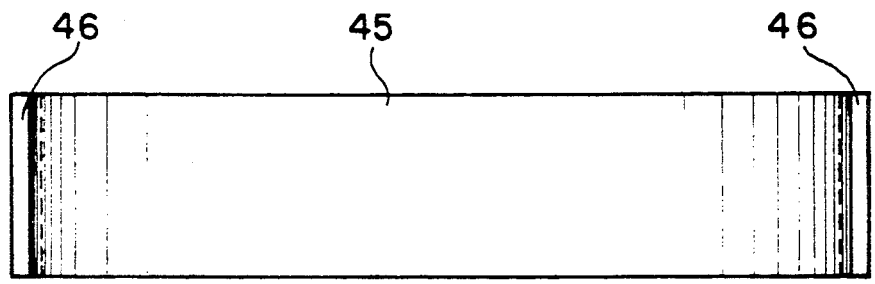
FIG. 4 is a top plan view of a device that is useful for relieving the pressure of clothing against an ostomy bag during use.
Figure 4A:
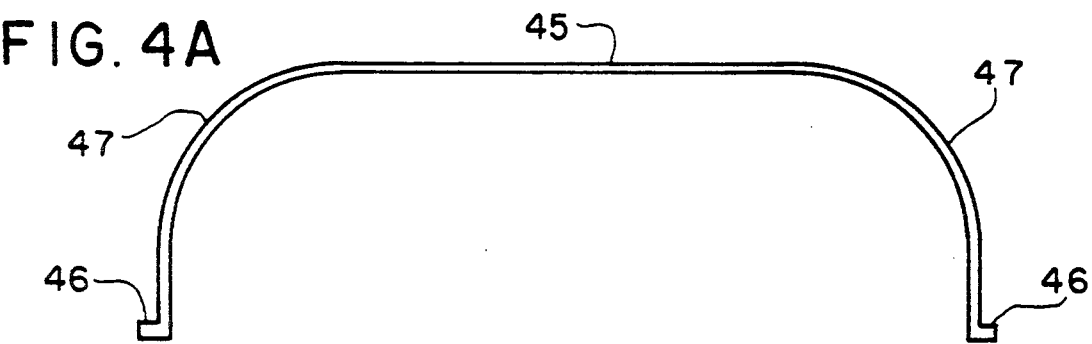
FIG. 4A is a longitudinal section view of the embodiment of FIG. 4.

FIG. 4 and FIG. 4A illustrate a device which can be held within the clamping rings of an ostomy appliance to hold the ostomy bag open, even when the user is in a sitting position, against the pressure of clothing on the outer portions of the ostomy bag. The device can be used without interference with the normal operation of the ostomy bag and avoid the collapse of the bag against the opening from the stoma. In basic form, it is an open, arched member provided with lip-portion at its extremities to permit holding within the coupling members. It may be formed by the junction of several arched members so long as sufficient open area is provided to permit passage of fluids. In its simplest form, the device comprises a flexible, semi-rigid strip of material which has been formed into a U-shape, either permanently or by flexing at the time of insertion. Strip 45 is provided with lips 46 and shoulders 47 to define the generally U-shaped device. The lip portion 46 should be of a width and thickness sufficient to be held within the coupling members of the ostomy appliance without interfering with the coupling action. The shoulders 47 should be separated from each other by a distance approximately equal to the smallest coupling opening so as to ensure that there will be no interference with the normal flow of fluids into the ostomy bag. The shoulder and the lip should be separated from each other by a distance sufficient to extend beyond the coupling device and, preferably, two to three times the height of the coupling device so that the ostomy bag will be kept adequately open to function. The device 45 should be sufficiently rigid to hold the bag open and away from the wearer, but at the same time must be able to withstand the routine impacts that will be encountered when a user is wearing the ostomy appliance with the device in place.

Figure 4B:
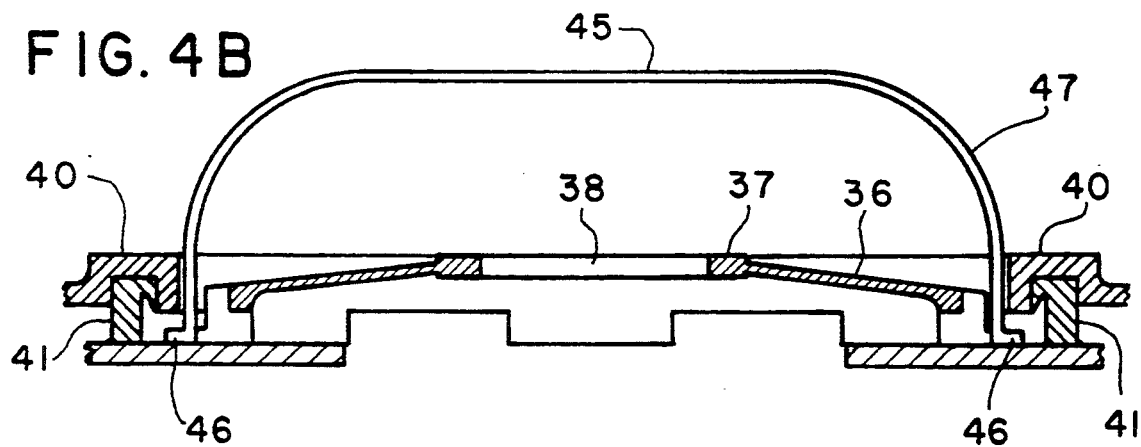
FIG. 4B is a plan view of an ostomy appliance in which the embodiment of FIG. 4

FIG. 4B shows the device of FIG. 4 and FIG. 4A used in combination with the device of FIG. 3 and FIG. 3A. Like parts are given like numbers from those figures. The width of device 45 and, more particularly of lip 46, is such that it will fit into the spaced opening 39 of the device in FIG. 3. In the ideal case, the overall width of the lip corresponds to that of the open space, or just slightly under to permit smooth insertion and the thickness of lip 46 is essentially the same as the thickness of lip 35. Thus, when the clamping rings 40 and 41 are in place, they will hold the device of FIG. 3 and the device of FIG. 4 in a smooth, tight fit, permitting simultaneous use of both devices with the combined advantage to the user.

Figure 5A:
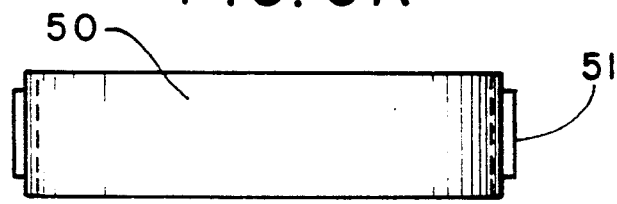
FIG. 5A is a top plan view of a second embodiment of the device for relieving the pressure of clothing against an ostomy bag during use.
Figure 5B:
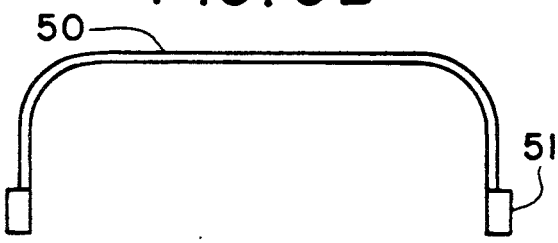
FIG. 5B is a longitudinal section view of the embodiment of FIG. 5A.
Figure 5C:
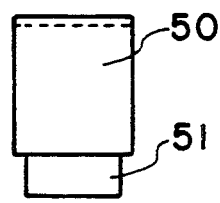
FIG. 5C is an end view of the device as shown in FIG. 5B.
Figure 5D:
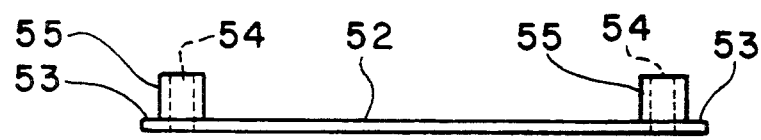
FIG. 5D is a longitudinal section view of a support ring to be used for holding the device of FIGS. 5A–5C in place within coupling rings of an ostomy appliance.
Figure 5E:
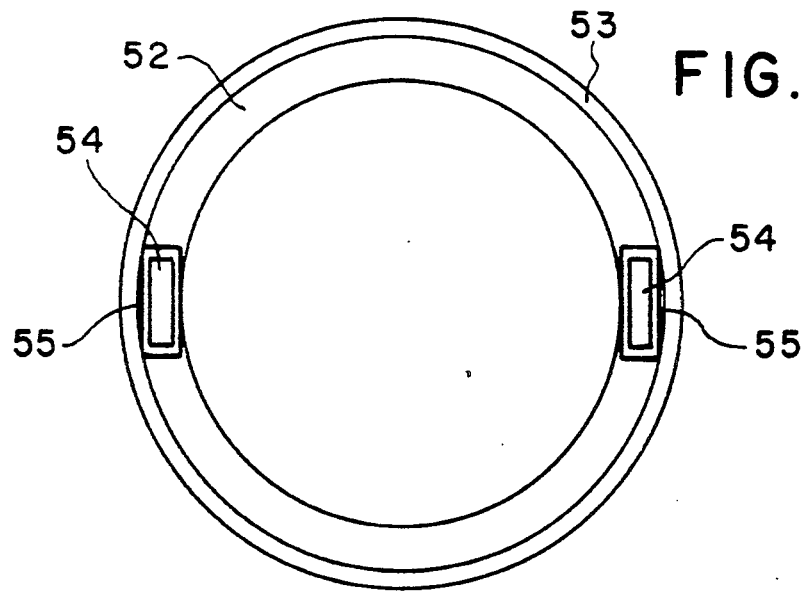
FIG. 5E is an elevation view of the support member of FIG. 5D.

FIGS. 5A through 5E show an alternative embodiment of the device which may be utilized to maintain the ostomy bag open, even when the wearer is in a seated position, with clothing pressing against the outer surface of the bag. The device comprises two basic parts, a flexible semi-rigid strip of material shown in FIGS. 5A through 5C and a support ring shown in FIGS. 5D and 5E. The strip member 50 is shown in a generally U-shaped form in FIG. 5B. While the device can be preformed into that shape, it is also possible to use a flat strip of material that is sufficiently flexible to be easily bent into the U-shaped position for insertion in the support member of FIGS. 5D and 5E. As shown, the strip member consists of the main body having a lip portion 51 which can be an extended portion of the main body of strip 50 or may be simply a flush insert tab. As shown in FIGS. 5D and 5E, the support ring 52 is provided with lips 53, to be gripped by coupling rings of the ostomy appliance in the manner previously indicated. The ring is also provided with slots 54 to receive insert portions 51 of the strip shown in FIGS. 5A through 5C. As will be apparent from FIG. 5D, the slots 54 are preferably inserted in a raised portion 55 to reduce the tendency of insert portions 51 from extending through support ring 52 in a manner to cut or irritate the wearer.

The device of FIG. 5A through 5E may be made sufficiently thin, particularly if the lip portions of the devices of FIGS. 1 through 3 are also made sufficiently thin, that both devices may be used simultaneously by placing the device of FIGS. 5A through 5E on top of the device of FIGS. 1 through 3. By "on top of", it is intended to refer to a position further removed from the wearer of the ostomy appliance than the underlying device.

While in the foregoing embodiment of the invention there has been considerable disclosure of detail for purposes of illustration, it will be understood by those skilled in the art that many of these details may be varied without departing from the spirit and scope of the invention.

What is claimed is:

1. In an ostomy appliance comprising a body-side faceplate assembly and a pouch assembly wherein each of said assemblies is provided with a flange member having a coupling member affixed thereto for the coupling of said faceplate assembly and pouch assembly into a single ostomy appliance, the improvement which comprises in combination with said assemblies of a concave disk insert having a circumferential lip portion adapted to be held by and between said coupling rings and having an outer diameter greater than the inner diameter of the smaller of the coupling rings, but less than the outer diameter of the larger of the coupling rings to permit placement of said concave disk between said coupling rings, said concave disk insert having a height such that the disk will not protrude substantially beyond the coupling rings into the ostomy bag, but not so flat as to touch the stoma of the wearer when the stoma is in its normal condition, said concave disk insert provided with a central opening having a diameter in the range of about one-half inch up to about three-fourths of an inch.

2. An improved ostomy appliance in accordance with claim 1 in which the said concave disk insert is provided with a reinforcing ring in surrounding relation to said central opening.

3. An improved ostomy appliance in accordance with claim 2 in which said circumferential lip portion comprises a continuous circumferential ring adapted to lie flat within the plane of junction of said coupling rings and integral with the concave portion of the concave disk insert and in which said concave portions are further provided with openings intermediate said lip portion and said reinforcing ring to improve the ease of cleaning of said concave disk insert.

4. An improved ostomy appliance in accordance with claim 2 in which said circumferential lip portion comprises a plurality of lips in spaced relation to each other around the circumference of said disk insert, said lips adapted to lie within the plane of said junction of said coupling rings and integral with the concave portion of the concave disk insert to provide openings intermediate said lip portion and said reinforcing ring to improve the ease of cleaning of said concave disk insert.

5. In an ostomy appliance comprising a body-side faceplate assembly and a pouch assembly wherein each of said assemblies is provided with a flange member having a coupling member affixed thereto for the coupling of said faceplate assembly and pouch assembly into a single ostomy appliance, the improvement which comprises in combination with said assemblies of a means for holding the exterior wall of said pouch assembly apart from the opening to the stoma of the wearer comprising a semirigid, flexible member having lip portions adapted to be held by and between said coupling rings to permit placement of said member between said coupling rings, said semirigid, flexible member adapted to be placed in an arched position away from the body-side faceplate assembly while being held by and within said coupling of said coupling members, the arch of said arched member having a height substantially greater than the thickness of said coupling.

6. An improved ostomy appliance in accordance with claim 5 in which said arched member comprises a single strip of material comprising a body portion and a lip portion at each end of the body portion adapted to permit the insertion of said lip portions between the coupling rings of said coupling with the body portion of said strip in a generally U-shaped form extending through the coupling ring of said pouch assembly a sufficient distance to urge the exterior wall of said pouch assembly away from said coupling ring.

7. In an ostomy appliance comprising a body-side faceplate assembly and a pouch assembly wherein each of said assemblies is provided with a flange member having a coupling member affixed thereto for the coupling of said faceplate assembly and pouch assembly into a single ostomy appliance, the improvement which comprises in combination with said assemblies of the further combination of (A) a concave disk insert having a circumferential lip portion adapted to be held by and between said coupling rings and having an outer diameter greater than the inner diameter of the smaller of the coupling rings, but less than the outer diameter of the larger of the coupling rings to permit placement of said concave disk between said coupling rings, said concave disk insert having a height such that the disk will not protrude substantially beyond the coupling rings into the ostomy bag, but not so flat as to touch the stoma of the wearer when the stoma is in its normal condition, said concave disk insert provided with a central opening having a diameter in the range of about one-half inch up to about three-fourths of an inch and (B) a means for holding the exterior wall of said pouch assembly apart from the opening to the stoma of the wearer comprising a semirigid, flexible member adapted to be placed in an arched position away from the body-side faceplate assembly while being held by and within said coupling of said coupling members, the arch of said arched member having a height substantially greater than the thickness of said coupling.

8. An improved ostomy appliance in accordance with claim 7 in which the said concave disk insert is provided with a reinforcing ring in surrounding relation to said central opening and in which said circumferential lip portion comprises a plurality of lips in spaced relation to each other around the circumference of said disk insert, said lips adapted to lie within the plane of said junction of said coupling rings and integral with the concave portion of the concave disk insert to provide openings intermediate said lip portion and said reinforcing ring to improve the ease of cleaning of said concave disk insert and in which said arched member comprises a single strip of material comprising a body portion and a lip portion at each end of the body portion adapted to permit the insertion of said lip portions between the coupling rings of said coupling with the body portion of said strip in a generally U-shaped form extending through the coupling ring of said pouch assembly a sufficient distance to urge the exterior wall of said pouch assembly away from said coupling ring, the width of said lip portions of said arched member and the space between the lip portions of said concave disk insert corresponding to permit insertion of said concave disk insert and said arched member into said ostomy appliance with said lip portions lying in generally the same plane corresponding generally to the point of junction of the coupling rings.

* * * * *